US012745982B2

(12) United States Patent
Kaneko et al.

(10) Patent No.: US 12,745,982 B2
(45) Date of Patent: Sep. 29, 2026

(54) LEARNING MODEL, STORAGE MEDIUM STORING DIAGNOSTIC PROGRAM, ULTRASONIC DIAGNOSTIC APPARATUS, ULTRASONIC DIAGNOSTIC SYSTEM, IMAGE DIAGNOSTIC APPARATUS, MACHINE LEARNING APPARATUS, LEARNING DATA CREATION APPARATUS, LEARNING DATA CREATION METHOD, AND STORAGE MEDIUM STORING LEARNING DATA CREATION PROGRAM

(71) Applicant: Konica Minolta, Inc., Tokyo (JP)

(72) Inventors: Shikou Kaneko, Niiza (JP); Hiroaki Matsumoto, Yokohama (JP); Akihiro Kawabata, Hachioji (JP); Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 72 days.

(21) Appl. No.: 18/348,592

(22) Filed: Jul. 7, 2023

(65) Prior Publication Data

US 2024/0008853 A1 Jan. 11, 2024

(30) Foreign Application Priority Data

Jul. 8, 2022 (JP) ................................. 2022-110177

(51) Int. Cl.
*A61B 8/00* (2006.01)
*G06T 7/50* (2017.01)
(Continued)

(52) U.S. Cl.
CPC .................. *A61B 8/48* (2013.01); *G06T 7/50* (2017.01); *G06T 7/62* (2017.01); *G16H 50/20* (2018.01); *G06T 2207/10132* (2013.01)

(58) Field of Classification Search
CPC .......... G06T 2207/20084; G06N 20/00; A61B 8/48; A61B 8/5207; A61B 8/52
See application file for complete search history.

(56) References Cited

U.S. PATENT DOCUMENTS

2014/0036091 A1* 2/2014 Zalev .................. A61B 8/4444 348/163
2014/0212014 A1* 7/2014 Kim .......................... G06T 3/14 382/131
(Continued)

FOREIGN PATENT DOCUMENTS

| | | | |
|---|---|---|---|
| JP | 2020-114302 | A | 7/2020 |
| JP | 2020-519369 | A | 7/2020 |
| WO | 2021/199966 | A1 | 10/2021 |

OTHER PUBLICATIONS

Notice of Reasons for Refusal dated Oct. 29, 2024, issued for the corresponding Japanese Patent Application No. 2022-110177, 9 pages, with English translation.
(Continued)

*Primary Examiner* — Anne M Kozak
*Assistant Examiner* — Kaitlyn Eunji Kim
(74) *Attorney, Agent, or Firm* — LUCAS & MERCANTI, LLP

(57) ABSTRACT

A non-transitory storage medium storing a computer-readable diagnostic program that causes a computer to execute outputting that is outputting a first inference result from third ultrasonic image data before processing including coordinate transformation based on a reception signal for image generation received by an ultrasonic probe by using a learning model. The learning model is machine-learned using learning data formed with a pair of: first ultrasonic image data based on a reception signal for image generation received by an ultrasonic probe; and second correct answer data obtained by performing inverse transformation of coor-
(Continued)

dinate transformation on first correct answer data for second ultrasonic image data obtained by performing processing including coordinate transformation on the first ultrasonic image data.

20 Claims, 9 Drawing Sheets

(51) Int. Cl.
*G06T 7/62* (2017.01)
*G16H 50/20* (2018.01)

(56) References Cited

U.S. PATENT DOCUMENTS

| | | | | |
|---|---|---|---|---|
| 2018/0330518 | A1* | 11/2018 | Choi | G06T 7/62 |
| 2020/0234461 | A1* | 7/2020 | Osumi | G06T 7/136 |
| 2021/0219961 | A1* | 7/2021 | Toyonaga | G01S 15/895 |
| 2021/0251610 | A1* | 8/2021 | Stergiopoulos | A61B 8/5207 |
| 2023/0086332 | A1* | 3/2023 | Huang | A61B 8/488 600/437 |

OTHER PUBLICATIONS

Notice of Reasons for Refusal, dated Feb. 25, 2025, issued for the corresponding Japanese Patent Application No. 2022-110177, 9 pages, with English translation.

* cited by examiner

LEARNING MODEL, STORAGE MEDIUM STORING DIAGNOSTIC PROGRAM, ULTRASONIC DIAGNOSTIC APPARATUS, ULTRASONIC DIAGNOSTIC SYSTEM, IMAGE DIAGNOSTIC APPARATUS, MACHINE LEARNING APPARATUS, LEARNING DATA CREATION APPARATUS, LEARNING DATA CREATION METHOD, AND STORAGE MEDIUM STORING LEARNING DATA CREATION PROGRAM

REFERENCE TO RELATED APPLICATIONS

The entire disclosure of Japanese Patent Application No. 2022-110177 filed on Jul. 8, 2022, including description, claims, drawings and abstract is incorporated herein by reference in its entirety.

TECHNICAL FIELD

The present invention relates to a learning model, a storage medium storing a diagnostic program, an ultrasonic diagnostic apparatus, an ultrasonic diagnostic system, an image diagnostic apparatus, a machine learning apparatus, a learning data creation apparatus, a learning data creation method, and a storage medium storing a learning data creation program.

DESCRIPTION OF THE RELATED ART

Conventionally, many medical diagnoses are made on the basis of captured medical images. The medical image is output after being appropriately transformed into a display image of an appropriate coordinate system so as to be easily seen by a doctor or the like.

The diagnostic capabilities of doctors and the like using such medical images vary. Therefore, it is necessary to prevent oversight of an abnormality related to a disease or the like in the medical image. A technology in which a learning model related to image recognition using a neural network or the like is learned by machine learning and automatic determination of an image is performed is attracting attention. JP 2020-519369 A discloses a technique of using probability information obtained from an image using a machine learning algorithm for diagnosis of the image obtained using ultrasonic echoes.

SUMMARY OF THE INVENTION

In machine learning, an expert generates correct answer data (teacher data). The teacher data is input to a learning model together with learning data to cause the learning model to learn. At this time, if image data on which processing such as the above-described coordinate transformation has been performed is used in learning related to image recognition, since part of information included in the original image has been removed and the amount of information has decreased, there is a problem in that learning accuracy decreases.

An object of the present disclosure is to provide a learning model, a storage medium storing a diagnostic program, an ultrasonic diagnostic apparatus, an ultrasonic diagnostic system, an image diagnostic apparatus, a machine learning apparatus, a learning data creation apparatus, a learning data creation method, and a storage medium storing a learning data creation program, capable of obtaining a learning model with higher accuracy and using the learning model for diagnosis.

To achieve at least one of the abovementioned objects, according to an aspect of the present invention, a storage medium reflecting one aspect of the present invention is a non-transitory storage medium storing a computer-readable diagnostic program that causes a computer to execute outputting that is outputting a first inference result from third ultrasonic image data before processing including coordinate transformation based on a reception signal for image generation received by an ultrasonic probe by using a learning model, wherein the learning model is machine-learned using learning data formed with a pair of: first ultrasonic image data based on a reception signal for image generation received by an ultrasonic probe; and second correct answer data obtained by performing inverse transformation of coordinate transformation on first correct answer data for second ultrasonic image data obtained by performing processing including coordinate transformation on the first ultrasonic image data.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION

Hereinafter, embodiments of the present invention will be described with reference to the drawings. However, the scope of the invention is not limited to the disclosed embodiments.

Figure 1:
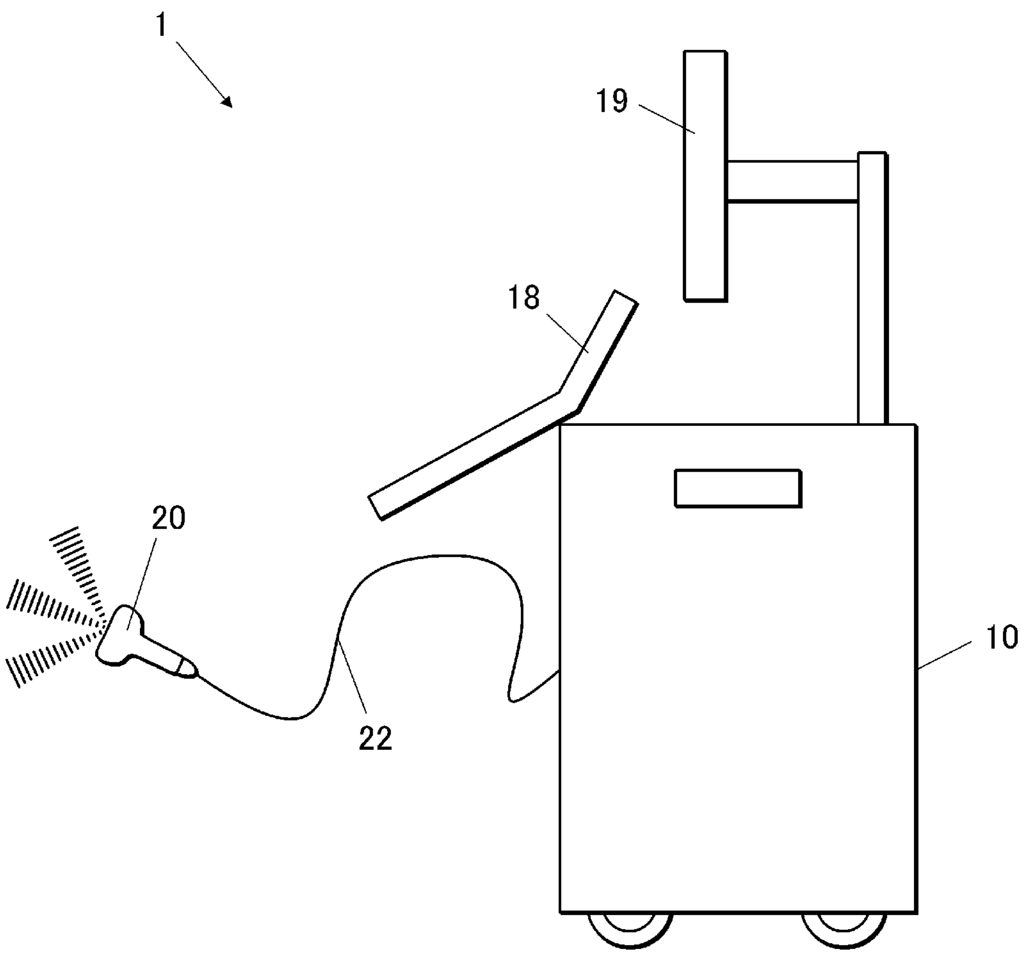
FIG. 1 is a view for explaining the arrangement of an ultrasonic diagnostic apparatus according to the present embodiment.

FIG. 1 illustrates a diagram for explaining a configuration of an ultrasonic diagnostic apparatus 1 (ultrasonic diagnostic system) according to the present embodiment. The ultrasonic diagnostic apparatus 1 includes a main body section 10 and an ultrasonic probe 20.

The ultrasonic probe 20 is a probe that transmits an ultrasonic wave to a subject and receives a reflected wave thereof. The ultrasonic probe 20 has piezoelectric members as a plurality of transducers. Each transducer is deformed by application of a voltage at an appropriate frequency to generate an ultrasonic wave. The ultrasonic probe 20 receives an ultrasonic wave by converting deformation of a transducer generated according to the input ultrasonic wave into an electric signal, and outputs the obtained electric signal as a reception signal for image generation. The ultrasonic probe 20 includes a signal cable 22. A connection terminal (not illustrated) located at one end of the signal cable 22 is connected to the main body section 10. Accordingly, an electric signal for transmitting an ultrasonic wave to be transmitted is transmitted from the main body section 10 to the ultrasonic probe 20, and a reception signal is transmitted from the ultrasonic probe 20 to the main body section 10.

The main body section 10 controls transmission and reception of the ultrasonic waves. The main body section 10 comprises an operation acceptance section 18 and a display part 19. The display part 19 displays the status and menu of the ultrasonic diagnostic apparatus 1, the captured image, the diagnosis result, and the like. The display part 19 includes, for example, a liquid crystal display (LCD) as a display screen, but is not limited thereto. The display part 19 may have a display screen of another system, for example, an organic EL display.

Figure 2:
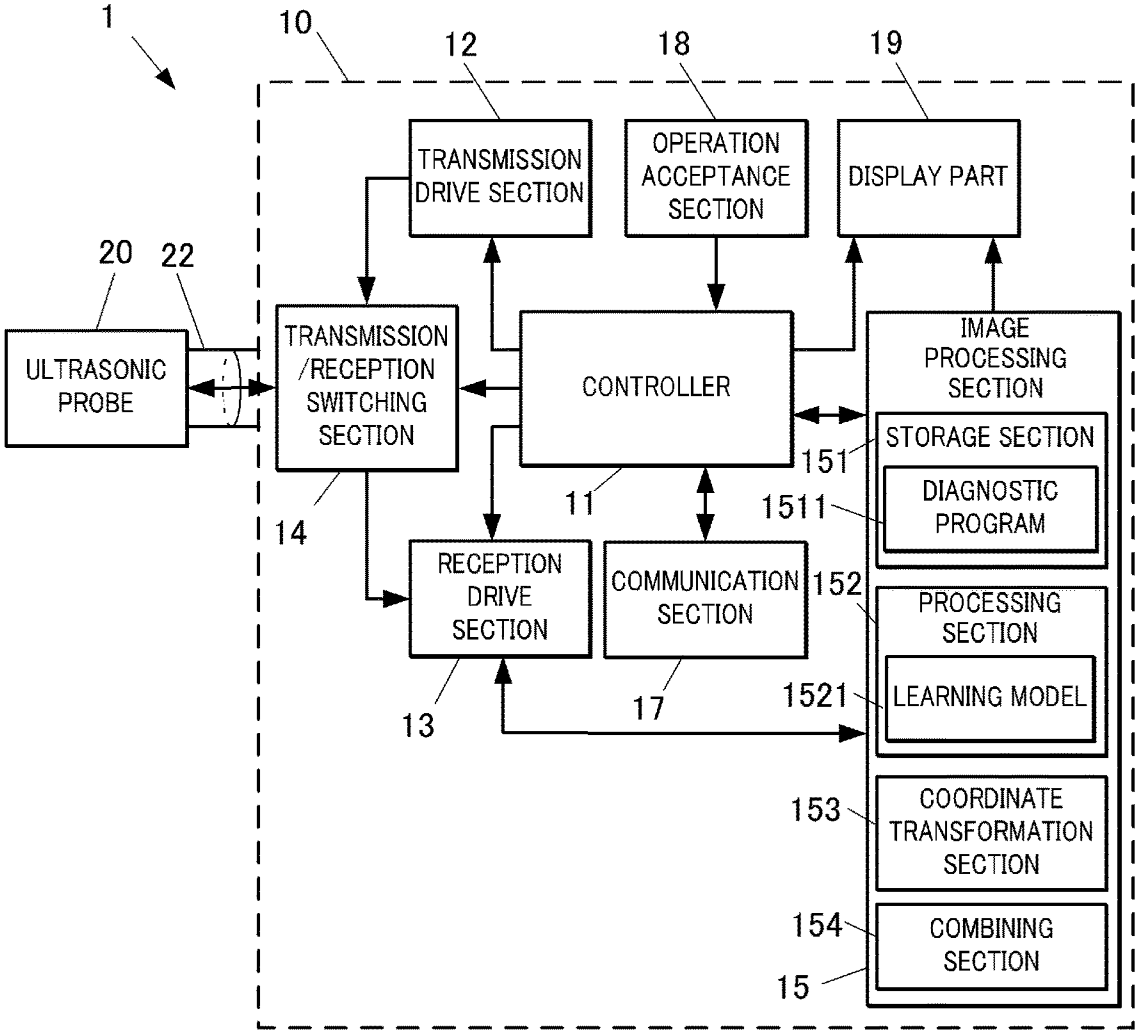
FIG. 2 is a block diagram illustrating a functional configuration of the ultrasonic diagnostic apparatus.

The operation acceptance section 18 accepts an input operation from the outside by a user or the like, and outputs an input signal indicating the content of the accepted input operation to the controller 11 (see FIG. 2). The operation acceptance section 18 may have a part or all of a keyboard, a keypad, a push-button switch, a slide switch, a toggle switch, a rocker switch, and the like.

FIG. 2 is a block diagram illustrating the functional configuration of the ultrasonic diagnostic apparatus 1.

The main body section 10 of the ultrasonic diagnostic apparatus 1 includes a controller 11, a transmission drive section 12, a reception drive section 13, a transmission/reception switching section 14, an image processing section 15, a communication section 17, an operation acceptance section 18, and a display part 19.

The transmission drive section 12 outputs a pulse signal to be supplied to ultrasonic probe 20, in accordance with a control signal input from controller 11. The ultrasonic probe 20 generates an ultrasonic wave based on the pulse signal. The transmission drive section 12 comprises, for example, a clock generation circuit, a pulse generation circuit, a pulse width setting section, and a delay circuit. The clock generation circuit is a circuit that generates a clock signal that determines the transmission timing and transmission frequency of the pulse signal. The pulse width setting section sets a waveform (shape), a voltage amplitude, and a pulse width of the transmission pulse output from the pulse generation circuit. The pulse generating circuit generates a transmission pulse on the basis of setting of the pulse width setting section, and outputs the transmission pulse to individual transducers of the ultrasonic probe 20 through different wiring paths. The delay circuit counts the clock signal output from the clock generation circuit. In a case where the delay circuit counts the lapse of the set delay time, the delay circuit causes the pulse generation circuit to generate a transmission pulse and outputs the transmission pulse to each wiring path.

The reception drive section 13 is a circuit that acquires the reception signal input from the ultrasonic probe 20 under the control of the controller 11. The reception drive section 13 includes, for example, an amplifier, an A/D conversion circuit, and a phasing addition circuit. The amplifier is a circuit that amplifies a reception signal corresponding to an ultrasonic wave received by each transducer of the ultrasonic probe 20 at a predetermined amplification factor set in advance. The A/D conversion circuit is a circuit that converts the amplified reception signal into digital data at a predetermined sampling frequency. The phasing addition circuit is a circuit that adjusts a time phase by giving a delay time to a wiring path corresponding to each transducer with respect to the A/D-transformed reception signal and generates sound ray data by adding these (phasing addition).

In a case in which ultrasonic waves are emitted (transmitted) from each transducer, the transmission/reception switching section 14 performs switching such that the transmission drive section 12 transmits a drive signal to the transducer on the basis of the control of the controller 11. On the other hand, based on the control of the controller 11, the transmission/reception switching section 14 performs switching so that the reception signal is output to the reception drive section 13 in a case where the signal corresponding to the ultrasonic wave emitted by the transducer is acquired.

The image processing section 15 generates a diagnostic image (second ultrasonic image) based on the reception data (reception signal) of the ultrasonic wave. The image processing section 15 includes a storage section 151, a processing section 152 (output section), a coordinate transformation section 153, and a combining section 154.

The processing section 152 acquires a signal by detecting (envelope detection) sound ray data (RF data) input from the reception drive section 13. The processing section 152 performs intermediate processing as necessary, for example, logarithmic amplification (logarithmic compression), sensitivity time control (STC), filtering (for example, low-pass processing, smoothing, dynamic filtering, and the like), emphasis processing, and the like. The processing section 152 may be capable of performing frequency analysis processing such as FFT Doppler (power Doppler) processing and color Doppler processing. The processing section 152 outputs the generated image (intermediate processed image).

The processing section 152 can detect a structure including an outer shape or the like of a detection target (target of interest) from the generated intermediate processed image, and can generate data for displaying the structure and characteristics so that a user can identify and recognize the structure and characteristics. In the detection of the structure of the detection target in the image processing section 15, the learning model 1521 (learned model) that has been machine-learned so as to detect the detection target from the input image is used. That is, in a case where an image for which a detection target is desired to be detected is input, the learning model 1521 detects a characteristic structure of the detection target from the image, and outputs a distribution of a probability (also referred to as a certainty degree) that each pixel position of the image is included in the structure. The processing section 152 may further obtain a contour line (boundary line between binary values) in a case where the probability is binarized with a certain threshold value from the output of the learning model 1521, and may convert the contour line into data that can be displayed so as to be superimposed on the diagnostic image. Alternatively, the processing section 152 may obtain characteristic values (physical quantities) of the structure to be detected, for example, a length (horizontal width), a width (vertical width), diameters (a diameter, a radius, a major axis, and a minor axis) of a circular or elliptical structure, an area, a centroid (center) position, a circumferential length, and a distance between specific positions of the structure. In a case where a three dimensional shape can be specified and estimated, the processing section 152 may obtain a volume, a surface area, a height, a depth, and the like. The generation and use of the learning model 1521 will be described in detail later.

Examples of the site to be detected and diagnosed by the ultrasonic diagnostic apparatus 1 include, but are not limited to, an lung; heart (heart wall; annulus end, etc); blood vessels such as the inferior vena cava (region; position); nerve and muscles. A fetus or the like can also be detected from the inspection image. Alternatively, not only the human body itself but also a medical instrument used for inspection, treatment, or the like, for example, a catheter and a puncture needle can be set as a detection target. Furthermore, these detection targets are not limited to detection of a specific state (a static state). Changes such as contraction/expansion of the detection and diagnosis target accompanying respiration or a pulse (a heartbeat) or the like may be specified. The learning model 1521 may be generated by learning for each detection target. A plurality of states corresponding to a change in a certain part may be detectable in the same learning model 1521.

The coordinate transformation section 153 performs processing (processing as digital scan conversion; DSC) for subjecting the intermediate processed image generated by the processing section 152 to coordinate transformation in accordance with the coordinates (each pixel position) of the display screen. For example, when outputting each frame image data in a B-mode display in which a two dimensional structure (internal structure of the subject) in a plane including a signal transmission direction (incident direction, depth direction of the subject) and a direction of the ultrasonic transmitted by the ultrasonic probe 20 (for one scanning cycle) is represented by an orthogonal coordinate system (Cartesian coordinate system) with the brightness signal according to the signal intensity as one of the diagnostic images, the coordinate transformation section 153 transforms the coordinate system of the original reception signal into the orthogonal coordinate system. The coordinate transformation will be described later. The coordinate transformation section 153 may be capable of performing image adjustment processing such as gamma correction in addition to the above. Alternatively, such processing may be performed by the processing section 152.

The image processing section 15 outputs the diagnostic image coordinate-transformed by the coordinate transformation section 153 to the display part 19 or the like. The diagnostic image may be output to the display part 19 as it is or may be returned to the processing section 152 once and output from the processing section 152 to the display part 19 or the like directly or after fine adjustment. For example, in a case where the characteristic value (physical quantity) as described above is measured and calculated based on a diagnostic image after coordinate transformation, the processing section 152 may measure and calculate the characteristic value (physical quantity) after coordinate transformation processing by the coordinate transformation section 153. When the diagnostic image is directly output from the coordinate transformation section 153 to the display part 19, the output process of the diagnostic image may be included in the configuration of the output section of the present disclosure.

The image processing section 15 includes a storage section 151. A program (diagnostic program 1511) for performing medical diagnosis by a doctor or the like using the diagnostic image and the output result of the learning model 1521 is stored in the storage section 151. The learning model 1521 may also be stored and retained in the storage section 151 and used by the processing section 152. The storage section 151 includes, for example, a nonvolatile memory such as a flash memory and/or a hard disk drive (HDD).

The combining section 154 combines a plurality of images by performing processing such as alignment and weighting when combining and outputting a plurality of images after intermediate processing including coordinate transformation along with spatial compounding, frequency compounding, time averaging, and/or smoothing. In addition, the combining section 154 may be able to combine or decompose the probability distribution image output by the learning model 1521 as in a modification example described below.

The image processing section 15 may comprise a dedicated CPU and RAM used for generating (image processing) the diagnostic image, the output image of the learning model 1521, and the like as a controller. The image processing section 15 may further include a graphics processing unit (GPU) that performs image processing. In the image processing section 15, a dedicated hardware configuration for image generation may be provided by being formed on a substrate (an application-specific integrated circuit (ASIC) or the like). The image processing section 15 may have a configuration in which an image generation process is performed by the CPU and the RAM of the controller 11. The processing by the processing section 152, the processing by the coordinate transformation section 153, and the processing by the combining section 154 may be performed by a common CPU (hardware processor), or hardware processors may be individually assigned.

The communication section 17 controls communication with the outside in accordance with a predetermined communication rule (protocol). The communication protocol includes, for example, a protocol related to a LAN (TCP/IP or the like). The communication section 17 can, for example, transmit a diagnostic image to and receive a learned machine learning model from the electronic calculator 40 to be described later.

The operation acceptance section 18 includes a push button switch, a keyboard, a mouse, a track ball, a touch screen positioned to overlap a display screen, or a combination thereof. The operation acceptance section 18 generates an operation signal having a content corresponding to a user's input operation, and outputs the operation signal to the controller 11.

The display part 19 includes a display screen of any of various display systems such as an LCD (Liquid Crystal Display), an organic EL (Electro-Luminescent) display, an inorganic EL display, a plasma display, and a CRT (Cathode Ray Tube) display, and a drive section thereof. The display part 19 drives the display screen (each display pixel) in accordance with the control signal output from the controller 11 and/or the image data generated by the image processing section 15. The display part 19 displays, on the display screen, a menu related to the ultrasonic diagnosis, a status, a captured image and a diagnostic result based on the received ultrasonic wave, and the like. The display part 19 may be configured to separately comprise an LED lamp or the like and visually notify the presence or absence of power supply, an operation abnormality, or the like.

The operation acceptance section 18 and the display part 19 may be integrated with the housing of the main body section 10. Alternatively, the operation acceptance section 18 and the display part 19 may be an peripheral or an external device which is attached to the main body section 10 via an RGB cable, a USB cable, an HDMI cable (registered trade mark: HDMI) or the like. In a case where the main body section 10 is provided with the operation input terminal and the display output terminal, the peripheral device for operation acceptance and the peripheral device for display may be respectively connected to these terminals.

The ultrasonic probe 20 functions as an acoustic sensor that oscillates ultrasonic waves (here, about 1 to 30 MHz) and emits the ultrasonic waves to a subject such as a living body and receives reflected waves (echoes) reflected by the subject among the emitted ultrasonic waves and converts the reflected waves into electric signals. This ultrasonic probe 20 includes an array of a plurality of transducers for transmitting and receiving ultrasonic waves, a signal cable 22, and the like.

The signal cable 22 has a connector (not illustrated) with the main body section 10 at one end. The ultrasonic probe 20 is attachable to and detachable from the main body section 10 by the signal cable 22. A user brings an ultrasonic wave transmission/reception surface of the ultrasonic probe 20 into contact with a subject under an appropriate pressure and operates the ultrasonic diagnostic apparatus 1 to perform ultrasonic diagnosis.

Some ultrasonic probes 20 are capable of emitting ultrasonic waves by any one of linear scanning (straight traveling), sector scanning (radial scanning), convex scanning (fan-shaped scanning), arc scanning (bow-shaped scanning), and the like, or a plurality of these methods (order and direction). Furthermore, the ultrasonic probe 20 itself also has structural types in which transducers are arranged on a plane (linearly) or arranged in a fan shape (convexly) on a curved surface, according to these scanning methods. An appropriate ultrasonic probe 20 may be selected and connected to the single main body portion 10 according to the use or the like, and ultrasonic waves may be transmitted and received by an appropriate scanning method.

Note that the main body section 10 and the ultrasonic probe 20 may be connected not by the wired signal cable 22 but by wireless communication means using infrared rays, radio waves, or the like.

On the other hand, in the present embodiment, the learning model 1521 is separately generated (learned) outside the ultrasonic diagnostic apparatus 1, and the created learning model is copied to the ultrasonic diagnostic apparatus 1. The learning data for learning is also created outside.

Figure 3:
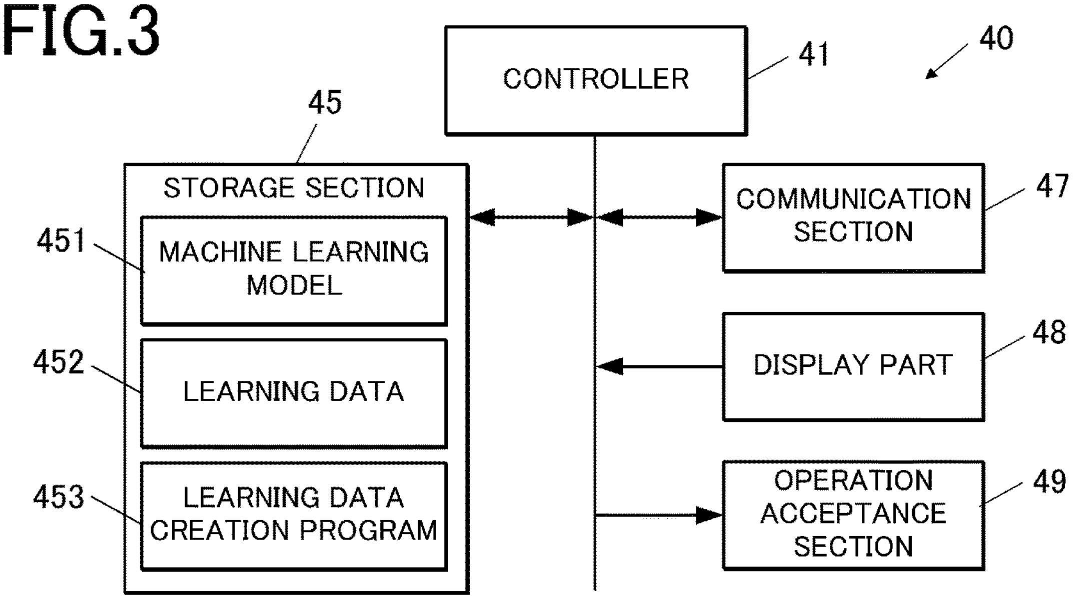
FIG. 3 is a block diagram showing a functional configuration of the electronic calculator.

FIG. 3 is a block diagram illustrating a functional configuration of the electronic calculator 40 that is the machine learning apparatus and the learning data creation apparatus of the present embodiment.

The electronic calculator 40 may be a general PC (computer), and includes a controller 41, a storage section 45, a communication section 47, a display part 48, and an operation acceptance section 49.

The controller 41 has a hardware processor that performs arithmetic processing to integrally control the overall operation of the electronic calculator 40. The hardware processor nay include a logic circuit configured to perform a specific process, for example, an application specific integrated circuit (ASIC), in addition to a central processing unit (CPU) and a random-access memory (RAM).

The storage section 45 includes a nonvolatile memory. The nonvolatile memory may include a hard disk drive (HDD) in addition to a flash memory and the like. The storage section 45 may include, in addition to the nonvolatile memory, a volatile memory (such as DRAM) for temporarily storing large-capacity image data and intermediate processed data thereof. The storage section 45 stores a machine learning model 451 and learning parameters thereof, learning data 452 for learning the machine learning model 451, and a learning data creation program 453 for controlling processing for creating the learning data 452. The machine learning model 451 receives an input of a signal ultrasonically measured in the ultrasonic diagnostic apparatus 1 and detects (infers) and outputs the presence or absence, position, structure, and the like of a detection target (target of interest) in the subject. The learning of the machine learning model 451 is here supervised learning. That is, the learning data 452 includes image data that is input data and teacher data (correct answer data) associated with each image data.

The communication section 47 controls communication with the outside according to a predetermined communication protocol. The communication protocol includes a network communication protocol in a LAN or the like, and the communication section 47 includes a network card corresponding to the communication protocol.

The display part 48 has a display screen and displays various contents on the display screen based on the control of the controller 41. The display screen is, for example, a liquid crystal display (LCD), but is not limited thereto.

The operation acceptance section 49 accepts an input operation from the outside and outputs an operation signal corresponding to the content of the accepted input operation to the controller 41. The operation acceptance section 49 includes a pointing device such as a mouse. The operation acceptance section 49 may include a keyboard and/or a push-button switch in addition to the above. Instead of or in addition to these, the operation acceptance section 49 may include a touch screen or the like which is positioned to overlap the display screen of the display part 48.

Note that the display part 48 and the operation acceptance section 49 may be peripheral devices. The peripheral device may be connected to the connection terminal by a cable or the like according to any of various protocols or may be capable of wirelessly exchanging data by Bluetooth®, 2.4 GHz wireless communication, or the like.

Next, inference by the learning model 1521 and creation of learning data will be described.

As described above, the ultrasonic diagnostic apparatus 1 generates a measurement image on the basis of a signal received by the ultrasonic probe 20 and displays the measurement image. When displaying the measurement image, the ultrasonic diagnostic apparatus 1 may detect an object and a structure of a detection target and add display content that allows the detected object or the like to be identified. The ultrasonic diagnostic apparatus 1 may calculate parameters representing the position, size, and shape of the detected object and add the parameters to the display content. The learning model 1521 is used for detection of the detection target (estimation of the position range). The learning model 1521 is based on a known algorithm related to image recognition, and may be, for example, a model using a convolutional neural network (CNN).

The electronic calculator 40 that generates the learning model 1521 by causing the machine learning model 451 to learn (machine learning) creates the learning data 452 in advance before learning. The learning data 452 is obtained by adding teacher data (correct answer data) to image data which is an input target to the machine learning model 451 as described above. The teacher data defines, for example, a range (mask) of an object and a structure to be detected inside an image with respect to image data. This range is set by an expert (e.g., a doctor or a clinical technologist) who is skilled in the determination of results from ultrasonic medical images.

As described above, since various processing including coordinate transformation is performed on the measurement data in order to obtain a diagnostic image in the image processing section 15, part of information included in the original measurement data is missing or changed. As a result, accuracy and efficiency of learning may decrease in learning using a diagnostic image. In particular, in a case where the machine learning model 451 that detects a clinically meaningful structure is learned, a decrease in accuracy and efficiency is likely to be apparent. The machine learning model 451 is more likely to improve the accuracy of determination in learning using, as input data, an intermediate processed image (first ultrasonic image data) before a diagnostic image, in particular, before, during, or after intermediate processing other than coordinate transformation is performed, than in learning using a final diagnostic image.

On the other hand, an expert who sets teacher data usually views and uses only a final diagnostic image. Therefore, it is at least troublesome and often very difficult for an expert to directly set teacher data for an intermediate processed image. The electronic calculator 40 according to the present embodiment performs processing (intermediate processing) including coordinate transformation on an intermediate processed image (first ultrasonic image data) at a certain stage to acquire a diagnostic image (second ultrasonic image data) and obtains a position range (first correct answer data) of a correct answer set to the diagnostic image by an expert. The electronic calculator 40 specifies a position range (second correct answer data) of the correct answer in the intermediate processed image by performing inverse transformation of the coordinate transformation with respect to the position range of the correct answer. The electronic calculator 40 includes the specified position range as teacher data in the learning data (learning data for machine learning) in association with (as a pair with) the original intermediate processed image.

Figure 4:
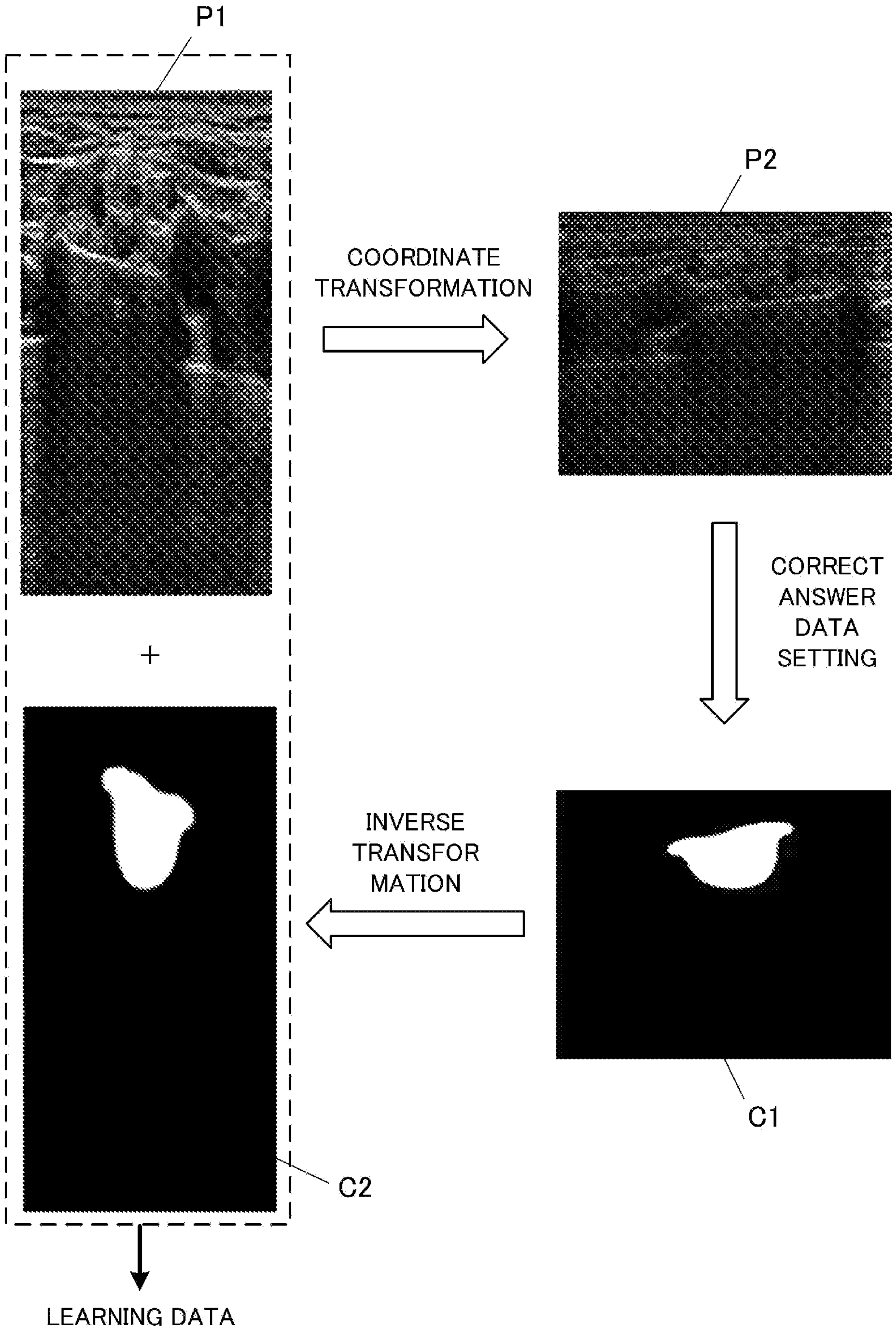
FIG. 4 is a diagram illustrating creation of learning data.

FIG. 4 is a diagram illustrating creation of learning data.

As usually performed in the ultrasonic diagnostic apparatus 1, the intermediate processed image P1 represented by the measurement coordinate system in which the measurement data is arranged as it is coordinate-transformed into a coordinate system for displaying an image, that is, an orthogonal (Cartesian) coordinate system, and is set as the diagnostic image P2. For example, in a case where sector scanning or convex scanning is performed by the ultrasonic probe 20 at the time of measurement, data of a diagnostic image in B mode is obtained in a polar coordinate system. Accordingly, the intermediate processed image P1 is subjected to coordinate transformation from the polar coordinate system to the rectangular coordinate system, and the diagnostic image P2 is obtained. In the polar coordinate system, since an acquisition density of data changes according to a value (a distance from the origin) in a radial direction, interpolation between pixels is performed in order to obtain data points (pixel values) at uniform intervals in the orthogonal coordinate system. In a case where linear scanning or the like is performed by the ultrasonic probe 20, measurement data is also obtained in the rectangular coordinate system in many cases. However, the aspect ratio on the data may not match the aspect ratio of the actual size. When the transmission/reception direction of the ultrasonic wave is set obliquely, two axes on the data may not be orthogonal to each other. Therefore, in these cases, the measurement data is subjected to affine transformation or projective transformation and is transformed into a diagnostic image represented by a rectangular coordinate system according to the actual aspect ratio. Between the intermediate processed image P1 and the diagnostic image P2, not only coordinate transformation but also the above-described various types of image processing for appropriately generating the diagnostic image P2 and making it easy to see may be included. These are collectively included in the processing including the coordinate transformation of the present embodiment.

The electronic calculator 40 may separately perform processing including the coordinate transformation in the same procedure as the ultrasonic diagnostic apparatus 1. Alternatively, the electronic calculator 40 may acquire a set (image set) of the intermediate processed image P1 and the diagnostic image P2 generated by the ultrasonic diagnostic apparatus 1 before and after the processing so that the electronic calculator 40 acquires the images before and after the processing including the coordinate transformation. The image acquired by the electronic calculator 40 may be only an image from a single ultrasonic diagnostic apparatus 1 or images from a plurality of ultrasonic diagnostic apparatuses 1.

The first correct answer data C1 is set for the diagnostic image P2 by an expert skilled in the result determination. The electronic calculator 40 may set a provisional correct answer range by applying a simple algorithm or the like for simply detecting a detection target to the diagnostic image P2. In a case where the range of the diagnostic image P2 and the provisional correct answer is set, the range is displayed by the display part 48, and the expert performs an operation of newly setting or correcting the range of the correct answer by the operation acceptance section 49 while viewing the diagnostic image P2, so that the first correct answer data C1 is generated (acquiring). Thereafter, the first correct answer data C1 is inversely transformed, and the second correct answer data C2 indicating the range of the correct answer in the same coordinate system as the intermediate processed image P1 is obtained (inverse transforming). In this case, the processes other than the coordinate transformation among the processes including the coordinate transformation may not be inversely transformed.

As described above, the parameter (matrix) of the coordinate transformation differs depending on the scanning method (sector scanning, convex scanning, or linear scanning) in the ultrasonic probe 20 and, as necessary, the type of the ultrasonic probe 20. Information on the type of probe used, phase information of scanning, and the like are provided to the diagnostic image P2 as supplementary information (transmission direction information) by an alpha channel such as metadata or header data. By referring to the supplementary information, it is specified with which transformation parameter the first correct answer data C1 should be inversely transformed.

The number of pieces of learning data 452 of the machine learning model 451 is not simply required to be large, and selection of data to be input to the machine learning model 451 is also important. For example, when there is a typical pattern that can occur as a structure to be discriminated, a person in charge or the like who can discriminate a structure to be detected may manually select a necessary number of pieces of image data at an appropriate ratio for each pattern from a large number of pieces of image data acquired in advance. The person in charge may be a person different from the expert and may have a lower degree of proficiency than the expert. An expert may set the above-described range of correct answers for the selected data, and the learning data 452 may be created from these. Before the manual selection, a large number of pieces of image data may be temporarily classified based on the setting of the provisional correct answer range.

The intermediate processed image P1 and the second correct answer data C2 are stored in association with each other (as a pair) in the learning data 452 of the storage section 45 (storage controlling).

Figure 5:
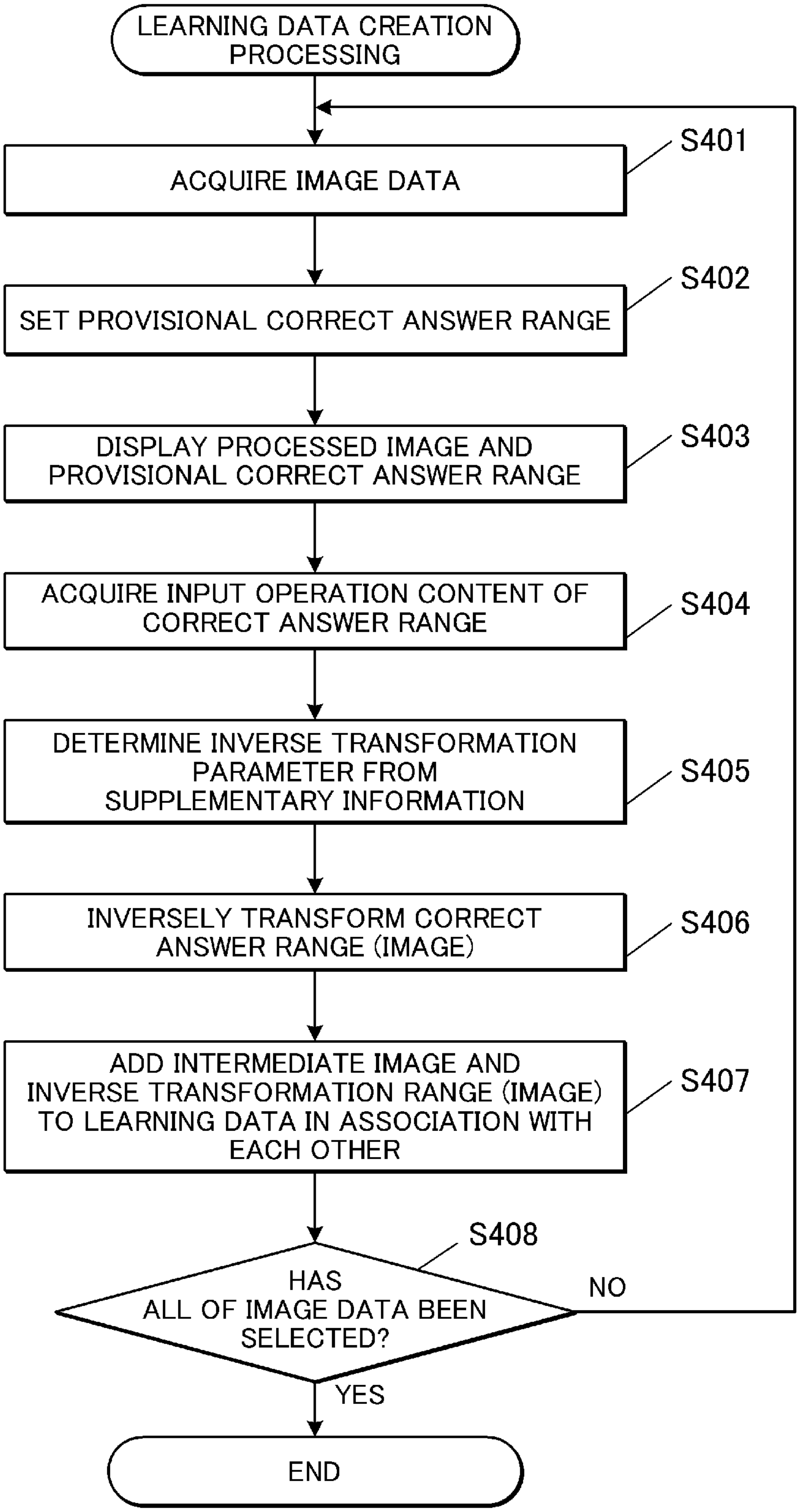
FIG. 5 is a flowchart showing a control procedure of the learning data creation processing.

FIG. 5 is a flowchart illustrating a control procedure by the controller 41 of the learning data creation processing executed by the electronic calculator 40. This learning data creation processing, which is the learning data creation method of the present embodiment, is started, for example, when the learning data creation program 453 is activated in response to a predetermined activation command by an input operation of the user of the electronic calculator 40. This input operation includes specification of a data set of measurement data to be used as learning data as described above.

When the learning data creation processing is started, the controller 41 acquires one unselected image from the designated dataset (step S401). The image data includes the intermediate processed image P1 and the diagnostic image P2.

The controller 41 sets a provisional correct answer range using a simple detection algorithm (step S402). The controller 41 allows the display part 48 to display the diagnostic image P2 and the provisional correct answer range (step S403). As described above, the processing of step S402 may not be performed. In this case, the controller 41 does not display the provisional correct answer range in the process of step S403. The controller 41 waits for the input operation by the operation acceptance section 49 and acquires information on the correct answer range of the target object to be the first correct answer data C1 based on the obtained content of the input operation (step S404). The processing of steps S401 and S404 constitutes an acquiring step (acquiring) of the learning data creation method (learning data creation program) of the present embodiment.

Controller 41 refers to the supplementary information of diagnostic image P2 and determines the inverse transformation parameters (transform matrix) of the coordinates according to the scanning method and phase, and if necessary, the type of ultrasonic probe 20 and the like (step S405). The controller 41 inversely transforms the acquired correct answer range of the first correct answer data C1 (step S406; inverse transforming). The inverse transformation parameters determined in step S405 are used for the inverse transformation. By this inverse transformation, the second correct answer data C2 indicating the correct answer range in the image range of the intermediate processed image P1 is obtained.

The controller 41 adds the obtained second correct answer data C2 and the intermediate processed image P1 to the learning data 452 in association with each other (step S407; storage controlling). The controller 41 additionally stores the learning data to be added in the learning data 452 of the storage section 45. The controller 41 determines whether all of the image data has been selected from the data set to be input (step S408). When it is determined that all the pieces of image data have not been selected, that is, there is unselected image data (step S408; NO), the controller 41 returns the processing to step S401. If it is determined that all the images have been selected (step S408; YES), the controller 41 ends the learning data creation processing.

In a case where the learning data 452 is generated, the machine learning model 451 is learned using the learning data 452. As is well known, machine learning is performed by, for example, feeding back a difference between an inference result with respect to an input of data to be learned and teacher data to a parameter. To be specific, the diagnostic image P2 of the learning data 452 is input to the machine learning model 451 to estimate (infer) the structure of the object. The result of the inference and the teacher data are compared with each other to obtain a difference (loss function) therebetween. The loss function is fed back (back-propagated) to the parameters.

Figure 6:
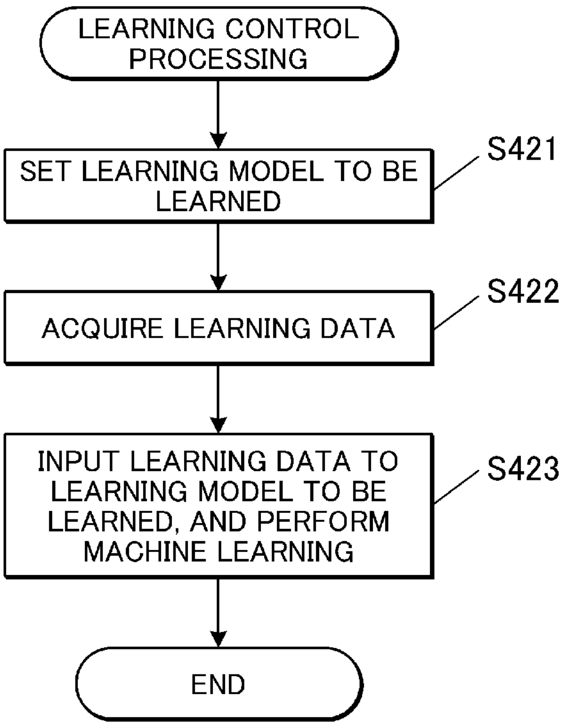
FIG. 6 is a flowchart illustrating a control procedure of learning control processing.

FIG. 6 is a flowchart illustrating a control procedure by the controller 41 of the learning control processing executed by the electronic calculator 40. This process is started in response to an input operation indicating a process start command to the operation acceptance section 49 by the user of the electronic calculator 40. This input operation includes an operation of designating the generated learning data 452 described above.

The controller 41 sets the machine learning model 451 to be learned (step S421). The controller 41 acquires the specified learning data 452 (step S422). The controller 41 sequentially inputs the learning data 452 to the machine learning model 451 to be learned. The controller 41 improves parameters on the basis of a comparison between the result outputted from the machine learning model 451 for the intermediate processed image P1 and the teacher data, to thereby cause machine learning to be performed (step S423). When all the data of the learning data 452 is input and the machine learning ends, the controller 41 ends the learning control processing.

The machine learning model 451 (learned model) that has been machine-learned is transmitted to the ultrasonic diagnostic apparatus 1 and is held as the learning model 1521. The learning model 1521 is used for estimation (inference) of a structure of a detection target from a measurement image based on a reception signal. Note that the learned model does not have to be sent directly to the ultrasonic diagnostic apparatus 1 from the electronic calculator 40. The learned model may be sent once to a management server or the like for managing the versions of the learned models and the like included in the plurality of ultrasonic diagnostic apparatuses 1. The management server may distribute the learned model by transmitting the learned model to the ultrasonic diagnostic apparatus 1.

Figure 7:
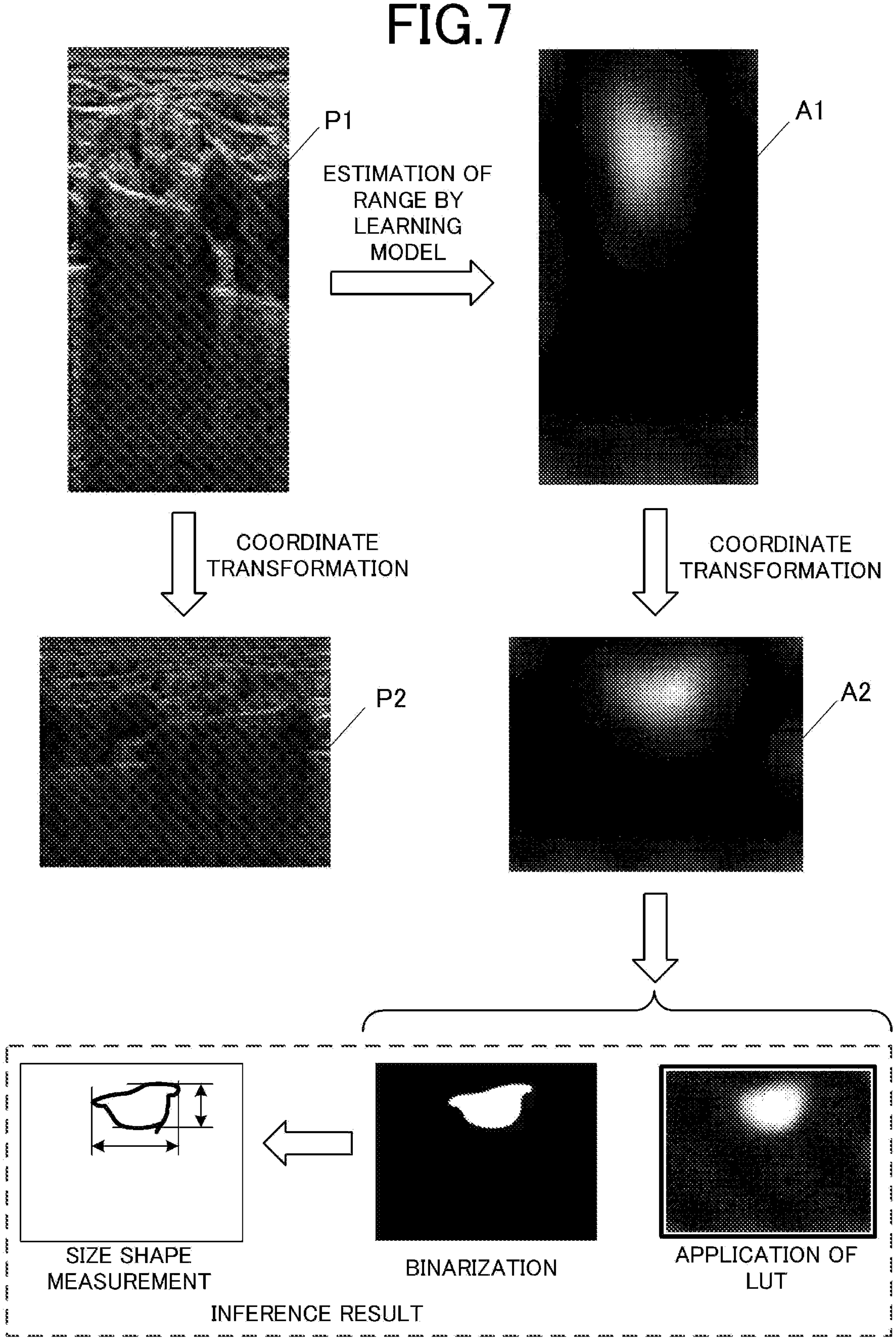
FIG. 7 is a view illustrating processing content by an image processing section.

FIG. 7 is a diagram for explaining processing contents by the image processing section 15 in the ultrasonic diagnostic apparatus 1. When a reception signal obtained by normal measurement by the ultrasonic probe 20 is input to the image processing section 15, the image processing section 15 generates an intermediate processed image P1 based on the reception signal.

The intermediate processed image P1 (third ultrasonic image data) is input to the learning model 1521. A probability distribution image A1 (first inference result) indicating a probability (certainty degree) that each pixel position is included in the structure of the detection target is output from the learning model 1521. The intermediate processed image P1 and the probability distribution image A1 are subjected to coordinate transformation to obtain a diagnostic image P2 and a probability distribution image A2 (second inference result) expressed in the same coordinate system as the diagnostic image P2. Transformation parameters of the coordinate transformation may be determined based on the supplementary information provided to the intermediate processed image P1. The supplementary information includes, as with the diagnostic image P2 described above, the scanning method and the phase of scanning, and if necessary, transmission direction information such as the type of the ultrasonic probe 20.

The probability distribution image A2 may be binarized with a predetermined threshold value according to content to be displayed on the display part 19 and settings. Alternatively, the luminance distribution of the probability distribution image A2 may be transformed (applied) with reference to a look-up table (LUT) for changing the luminance value distribution to a luminance value distribution easily viewable on the display screen. Based on the range of the structure specified by binarization, the characteristic value (physical quantity) of this structure may be measured and calculated. These processes are performed after the coordinate transformation. Accordingly, it is possible to suppress the occurrence of an adverse effect in which unnecessary noise is rather emphasized in the display content.

The display part 19 may display the inference result (second inference result) superimposed on the diagnostic image P2 or may display a part or all of the inference result in a window different from the diagnostic image P2.

The diagram 8A to the diagram 8C are diagrams illustrating a detection example of the target using the learning model 1521.

Figure 8A:
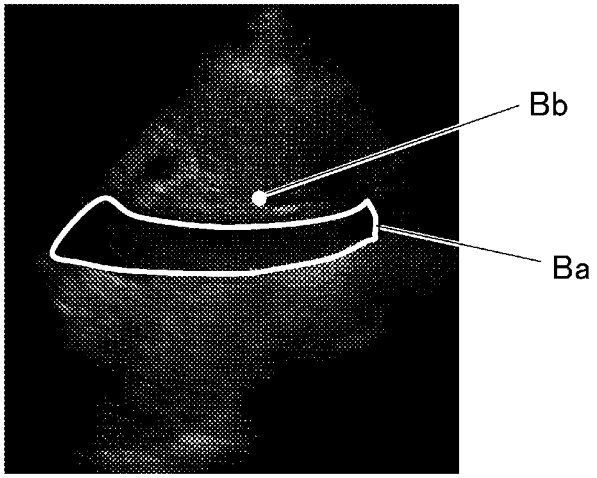
FIG. 8A is a diagram illustrating a detection example of a target using a learning model.
Figure 8B:
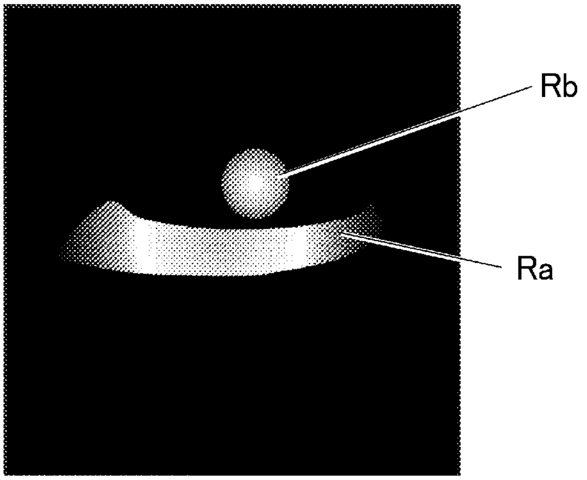
FIG. 8B is a diagram showing a detection example of a target using a learning model.
Figure 8C:
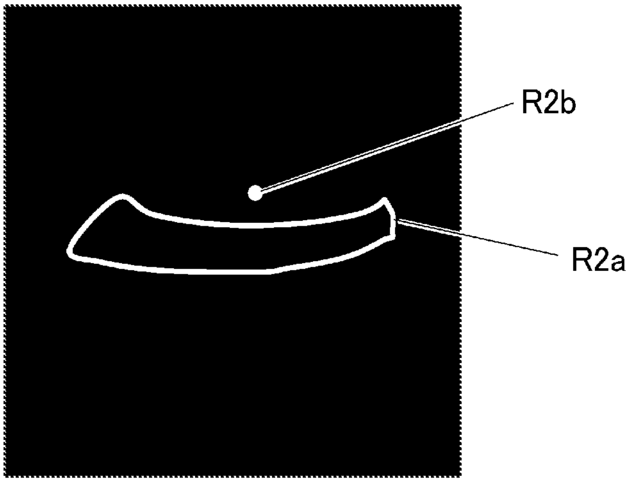
FIG. 8C is a diagram illustrating a detection example of a target using a learning model.

As shown in the diagnostic image of FIG. 8A, when the blood vessels near the liver including the inferior vena cava Ba and the hepatic veins Bb are imaged, the probability frequency distribution that each pixel is the inferior vena cava Ba and the hepatic veins Bb is obtained from the intermediate processed image by the learning model 1521. As shown in FIG. 8B, a region Ra with a high probability distribution, which is the range of the inferior vena cava Ba, and a region Rb with a high probability distribution, which is the range of the hepatic vein Bb, are shown. As illustrated in FIG. 8C, the contour R2*a* of the inferior vena cava Ba is obtained by comparing the probability distribution of the inferior vena cava Ba with an appropriate threshold value. A point showing the maximum value in the probability distribution of the hepatic vein Bb is obtained as a position R2*b* of the hepatic vein.

Figure 9:
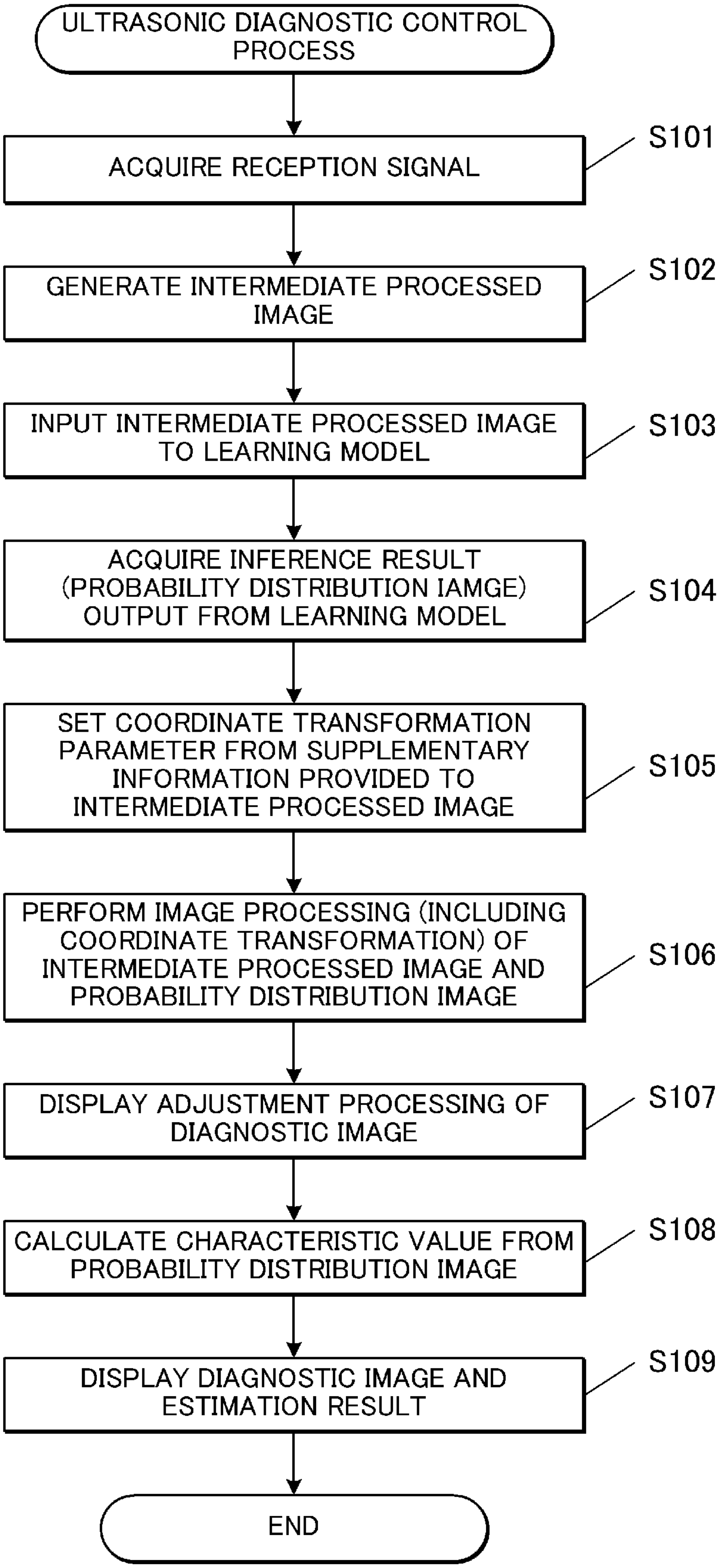
FIG. 9 is a flowchart illustrating a control procedure of an ultrasonic diagnostic control process.

FIG. 9 is a flowchart illustrating a control procedure by a controller of the image processing section 15 of an ultrasonic diagnostic control process executed in the ultrasonic diagnostic apparatus 1. The ultrasonic diagnostic control process is started when the diagnostic program 1511 is activated every time a reception signal from the ultrasonic probe 20 is input.

The image processing section 15 acquires data of the input reception signal (step S101). The image processing section 15 (processing section 152) generates an intermediate processed image P1 based on the reception signal (step S102).

The image processing section 15 (processing section 152) inputs the data of the intermediate processed image P1 to a machine learning model (step S103). The image processing section 15 acquires an inference result outputted from the learning model (step S104; outputting). The inference result includes a probability distribution image A1 representing the probability of being the range of the structure.

The image processing section 15 (coordinate transformation section 153) sets coordinate transformation parameters on the basis of the supplementary information on the intermediate processed image P1 and the display mode of the image (step S105). The image processing section 15 (the coordinate transformation section 153) performs image processing including a process of subjecting the intermediate processed image P1 and the probability distribution image A1 to coordinate transformation using the coordinate transformation parameters (step S106). The image processing section 15 performs processing for adjusting the display of the diagnostic image P2 obtained by the image processing, for example, gamma correction and contrast adjustment (step S107). The image processing section 15 calculates a characteristic value from the probability distribution image A2 after the coordinate transformation as necessary (step S108). The image processing section 15 causes the display part 19 to display the obtained diagnostic image P2 and the inference result (step S109). The image processing section 15 ends the ultrasonic diagnostic control process.

Note that although it has been described above that the reception signal from the ultrasonic probe 20 is processed substantially in real time, it is not limited to this. For example, the processing of steps S103, S104, S108, and the like may be omitted in the real-time processing, and the intermediate processed image P1 may be stored while the diagnostic image P2 is displayed in real time. When a clinical technologist, a doctor, or the like makes a diagnosis later, the processing in step S103 and subsequent steps may be executed using the stored intermediate processed image P1.

Modification Example

Although the intermediate processed image and the diagnostic image are described as being on a one to-one basis in the above embodiment, in medical diagnostics, a plurality of intermediate processed images are often combined after intermediate processing to obtain a final single diagnostic image. Such a case includes, for example, combining (spatial compounding) of images captured from a plurality of directions at a timing at which a temporal change in a plurality of intermediate processed images can be ignored, combining (frequency compounding) of captured images of the same range (capturing direction) by ultrasonic waves of a plurality of frequencies, simple superimposition and/or temporal smoothing of a plurality of captured images of the same frequency and the same range (capturing direction), and the like. Inference results obtained from individual intermediate processed images in such a case may also be combined after coordinate transformation. The combining may be, for example, a simple average of the inference results. Alternatively, the combining may be an average in which each inference result is weighted according to an imaging condition or the like of the intermediate processed image. In addition, even when the diagnostic image is not actually combined, an inference result (second inference result) obtained by transforming the coordinates of the inference results obtained from the plurality of intermediate processed images may be combined and displayed as an inference result common to the plurality of diagnostic images corresponding to the respective intermediate processed images. In a case where an inference result cannot be obtained with sufficient accuracy from one intermediate processed image even though the learning model 1521 is used, the inference result can be combined as described above. Thus, the accuracy is improved by increasing the S/N ratio of the inference result. As a result, it becomes easier for a doctor or the like to make a diagnosis using the inference result. The process of combining the inference result is performed by the combining section 154 of the ultrasonic diagnostic apparatus 1 together with the diagnostic image combining process.

Figure 10A:
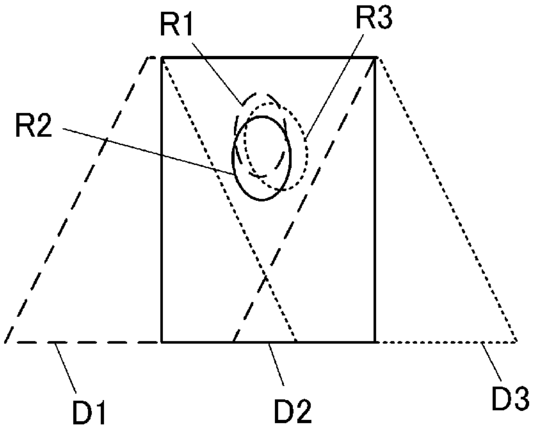
FIG. 10A is a diagram explaining an example of spatial compound.
Figure 10B:
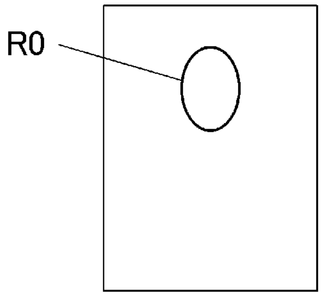
FIG. 10B is a diagram illustrating the setting of the teacher data for the spatial compound image.

FIG. 10A is a diagram explaining an example of spatial compound. FIG. 10B is a diagram illustrating generation of an inference result for a spatial compound image. The inference results T1 to T3 of the structure of the detection object respectively detected in the captured images D1 to D3 in the three directions illustrated in FIG. 10A can be combined and output as a single inference result TO illustrated in FIG. 10B.

On the contrary, in a case where the teacher data is generated with respect to the combined diagnostic image data to create the learning data 452, the teacher data may be inversely transformed into the coordinate systems of the plurality of intermediate processed images before being combined to obtain the teacher data represented by the coordinate systems of the plurality of intermediate processed images. This processing is performed by the controller 41 of the electronic calculator 40. That is, in the creation of the learning data 452, a plurality of intermediate processed images P1 corresponding to the diagnostic image P2 may be present. In this case, a plurality of pieces of second correct answer data C2 may be inversely transformed from the first correct answer data C1. Some or all of the inverse transformation parameters for obtaining the plurality of pieces of second correct answer data C2 may be different from each other.

Figure 11A:
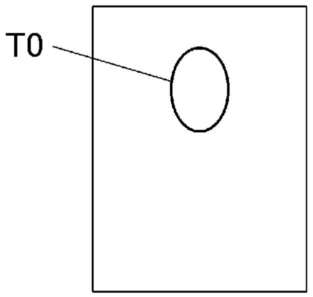
FIG. 11A is a diagram illustrating an example of the spatial compound image.
Figure 11B:
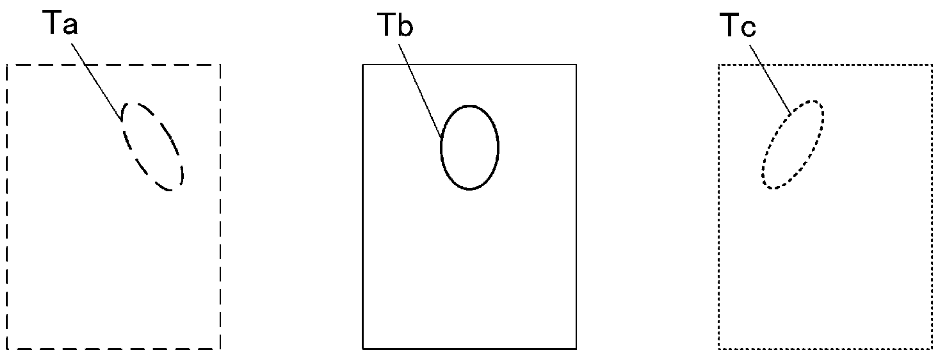
FIG. 11B is a diagram for explaining a setting example of the teacher data from the spatial compound image.

FIG. 11A is a diagram illustrating an example of the spatial compound image. FIG. 11B is a diagram for explaining a setting example of the teacher data from the spatial compound image. As illustrated in FIG. 11A, an inference result TO can be set for a single spatial compound image. As illustrated in FIG. 11B, the set inference result TO is decomposed according to the imaging directions of the plurality of images combined at the time of the generation of the spatial compound image, inverse transformation of the coordinate transformation is performed, and the images are divided into correct answer ranges Ta to Tc corresponding to the plurality (three) of intermediate processed images.

In such a case, all of the plurality of divided intermediate processed images may not be included in the learning data. For example, in the example of the 11B of the figure, only one or two intermediate processed images among three intermediate processed images may be set to be included in the teacher data. Correspondingly, teacher data inversely transformed only into a coordinate system corresponding to the one or two intermediate processed images may be obtained. The selected intermediate processed image may be an image captured in a fixed imaging direction with high accuracy in identifying the target in accordance with the direction. Alternatively, one of a predetermined number of intermediate processed images may be selected regardless of the imaging direction.

As described above, the learning model 1521 according to the present embodiment is machine-learned using learning data including a pair of the intermediate processed image P1 based on the reception signal for image generation received by the ultrasonic probe 20 and the second correct answer data C2 obtained by performing inverse transformation of coordinate transformation on the first correct answer data C1 for the diagnostic image P2 obtained by performing intermediate processing including coordinate transformation on the intermediate processed image P1.

As described above, since the learning model 1521 receives not the final diagnostic image P2 but the intermediate processed image P1 at the previous stage, it is possible to determine an image including a missing portion of information due to processing for making the diagnostic image P2 an image easy for a doctor or the like to see. Therefore, the learning model 1521 can output accurate inference with higher precision. Then, by using this learning model 1521 for ultrasonic diagnosis, more accurate diagnosis becomes possible. On the other hand, in a case where the learning data 452 used for learning the machine learning model 451 is created, it is difficult for a doctor or the like to directly apply a correct answer to an intermediate processed image P1 that the doctor or the like is not accustomed to and generate teacher data, and it takes time and effort even though the teacher data can be generated. Therefore, in the present embodiment, the first correct answer data C1 corresponding to the intermediate processed image P1 is obtained by inversely transforming the second correct answer data C2 in which the correct answer is provided to the diagnostic image P2. Accordingly, the machine learning model 451 can be easily learned, and the learning data 452 for obtaining the learning model 1521 capable of obtaining a more accurate output can be created.

The diagnostic image P2 may be a B-mode image. In general, in a B-mode image measured in time series in a polar coordinate system, the intermediate processed image P1 in the original polar coordinate system is greatly different in appearance from the diagnostic image P2. Accordingly, the first correct answer data C1 is provided to the diagnostic image P2 as described above and then the first correct answer data C1 is inversely transformed, whereby it is possible to obtain the learning data 452 particularly easily.

The coordinate transformation may include interpolation between pixels. In the measurement in the polar coordinate system as described above, the interval per predetermined azimuth angle changes according to the moving radius. Therefore, when each point is transformed into the diagnostic image P2 in the orthogonal coordinate system as it is, pixel points become uneven. In such a case, a uniform display image can be obtained by performing interpolation (in particular, linear interpolation) between pixels. Therefore, the diagnostic image P2 is easier for a user such as a doctor to view. Similarly, each point of the correct answer data provided to the diagnostic image P2 is appropriately represented by polar coordinates by interpolation after inverse transformation.

The coordinates of the first correct answer data C1 are inversely transformed based on the transmission direction information of the ultrasonic waves to obtain a second correct answer data C2. The scanning of the ultrasonic probe 20 is usually performed periodically. Therefore, by acquiring the scanning information appended to each (frame image) of the diagnostic images P2 as the transmission direction information of the ultrasonic wave, each pixel position of each diagnostic image P2 is easily specified. Therefore, the first correct answer data C1 can be easily transformed into the second correct answer data C2 based on the transmission direction information.

In particular, the transmission direction information of the ultrasonic wave is provided to a header or the like of the intermediate processed image P1 (and the diagnostic image P2). Therefore, it is possible to easily perform the coordinate transformation without separately acquiring information for the coordinate transformation and the inverse transformation.

Furthermore, the diagnostic program 1511 according to the present embodiment causes the computer to execute an outputting function of outputting a first inference result (probability distribution image A1) from ultrasonic image data (intermediate processed image P1) before intermediate processing (including coordinate transformation) based on a reception signal for image generation received by the ultrasonic probe 20 by using the learning model 1521 described above.

The diagnostic program 1511 using the learning model 1521 as described above is easily executed and causes the ultrasonic diagnostic apparatus 1 or a computer of an external electronic device to operate so as to detect a detection target (target of interest) more accurately. Therefore, the diagnostic program 1511 suppresses oversight of an abnormality or the like by a doctor. In addition, the diagnostic program 1511 can reduce the degree of dependence on the experience and ability of the doctor in the diagnosis and cause the doctor to perform a stable and more reliable diagnosis.

The ultrasonic diagnostic apparatus 1 of the present embodiment includes the ultrasonic probe 20 that transmits and receives ultrasonic waves to and from a subject, and the processing section 152 that outputs, using the learning model 1521 described above, a first inference result (probability distribution image A1) from ultrasonic image data (intermediate processed image P1) before intermediate processing (including coordinate transformation) based on a reception signal for image generation received by the ultrasonic probe 20.

According to the ultrasonic diagnostic apparatus 1, it is possible to quickly obtain a detection result with high accuracy from measurement data acquired using the ultrasonic probe 20.

The ultrasonic diagnostic apparatus 1 further includes a coordinate transformation section 153 that performs coordinate transformation on the first inference result, in particular, the probability distribution image A1 which requires or can be subjected to coordinate transformation to obtain a second inference result (probability distribution image A2). The processing section 152 outputs the second inference result after the coordinate transformation, for example, a probability distribution image A2 and/or a characteristic value based on the probability distribution image A2. The ultrasonic diagnostic apparatus 1 obtains data based on the original coordinate system, such as the probability distribution image A1, based on the image under processing as described above, and then performs the same coordinate transformation as that for the intermediate processed image P1 on this image (data). Therefore, the ultrasonic diagnostic apparatus 1 can obtain the inference result of the same coordinate system as the diagnostic image P2 with higher accuracy than the inference result that can be obtained by the learning model to which the diagnostic image P2 itself is input. In this case, when a result that does not require coordinate transformation is included in the first inference result, the coordinate transformation processing by the coordinate transformation section 153 may not be performed on the result.

Further, the ultrasonic diagnostic apparatus 1 includes a display part 19 capable of displaying the second inference result such as the probability distribution image A2. When the controller 11 causes the display part 19 to display the probability distribution image A2 represented in the same coordinate system as the diagnostic image P2, the user of the ultrasonic diagnostic apparatus 1, such as a doctor, can easily visually recognize and diagnose the detection result of the detection target with higher accuracy.

The ultrasonic diagnostic apparatus 1 further includes a combining section 154 that combines a plurality of probability distribution images A2 included in the second inference result. Even in the case of the learning model 1521 according to the present embodiment, the ultrasonic diagnostic apparatus 1 can obtain a detection result with higher accuracy by further combining a plurality of probability distribution images A2 that cannot be obtained with sufficient accuracy. In addition, the diagnostic image P2 may be an image in which a plurality of images such as a spatial compound image and a frequency compound image are originally combined and output. The combining section 154 can also perform combining of the probability distribution image A2 according to the combining of the plurality of images. Therefore, the ultrasonic diagnostic apparatus 1 can appropriately associate the detection result by the learning model 1521 with the diagnostic image P2.

Further, the processing section 152 may binarize or classify the second inference result such as the probability distribution image A2 and/or the characteristic value, or apply a look-up table for converting the value to the second inference result. The ultrasonic diagnostic apparatus 1 can further output the obtained second inference result as an image that is easier for the user to diagnose, a useful parameter, and the like. Accordingly, a doctor or the like can perform diagnosis more easily and accurately.

The processing section 152 may binarize the probability distribution image A2 included in the second inference result and estimate at least one of positions, areas, volumes, lengths, heights, widths, depths, and diameters associated with the target of interest (detection target) of the subject based on the binarized inference result. By specifying the range of the detection target by binarizing the probability distribution image in this way, the characteristic value can be easily obtained. In addition, as described above, since the probability distribution image is obtained with higher accuracy, the accuracy of the characteristic value itself is also improved.

Furthermore, the ultrasonic diagnostic system of the present embodiment includes the ultrasonic probe 20 that transmits and receives ultrasonic waves to and from the subject, and the processing section 152 that generates, using the learning model 1521 described above, the first inference result (probability distribution image A1) from the ultrasonic image data (intermediate processed image P1) before intermediate processing based on the reception signal for image generation received by the ultrasonic probe 20, and outputs the first inference result.

The ultrasonic diagnostic system may be configured by not a single ultrasonic diagnostic apparatus 1 but a combination of a plurality of apparatuses. Thus, a user can easily perform partial update, replacement, or the like of the above configuration.

Alternatively, the image diagnostic apparatus according to the present embodiment includes the processing section 152 that generates the first inference result (probability distribution image A1) from the ultrasonic image data (intermediate processed image P1) before intermediate processing based on the reception signal for image generation received by the ultrasonic probe 20 using the learning model 1521 and outputs the first inference result. That is, the main body section 10 may be treated as a separate body from the ultrasonic probe 20. As described above, since a plurality of types of ultrasonic probes 20 are attached and detached for replacement depending on the application or the like, the main body section 10 can be sold or lent separately from this, and thus each user can separately select and acquire a necessary ultrasonic probe 20.

The electronic calculator 40 as the machine learning apparatus of the present embodiment includes the controller 41 that performs machine learning of the machine learning model 451 using the learning data 452 including a pair of the intermediate processed image P1 based on the reception signal for image generation received by the ultrasonic probe 20, the correct answer data (probability distribution image A2) obtained by performing inverse transformation of the coordinate transformation on the correct answer data (probability distribution image A1) for the diagnostic image P2 obtained by performing intermediate processing including the coordinate transformation on the intermediate processed image P1, and the intermediate processed image P1 before the coordinate transformation. The electronic calculator 40 can obtain the learning model 1521 that can perform output with higher accuracy based on the intermediate processed image P1 including more information.

Further, the machine learning model 451 includes a convolutional neural network. That is, since the machine learning model 451 uses, as an algorithm, a CNN with which a stable and appropriate result can be easily obtained as image recognition processing, the learning model 1521 obtained through learning by the machine learning model 451 can detect a structure of a detection target or the like more reliably and accurately.

The electronic calculator 40 as the learning data creation apparatus of the present embodiment includes a controller 41 and a storage section 45. The controller 41 performs acquiring of acquiring first ultrasonic image data (intermediate processed image) based on a reception signal for image generation received by the ultrasonic probe 20 and first correct answer data (probability distribution image A1) for second ultrasonic image data (diagnostic image P2) obtained by performing intermediate processing including coordinate transformation on the first ultrasonic image data, inverse transforming of performing inverse transformation of the coordinate transformation on the first correct answer data (probability distribution image A1) to obtain second correct answer data (probability distribution image A2), and storage controlling of storing a pair of the first ultrasonic image data (intermediate processed image) before the intermediate processing and the second correct answer data (probability distribution image A2) in the storage section 45 as learning data for machine learning.

With this electronic calculator 40, the learning data 452 described above can be appropriately created.

Further, the learning data creation method of the present embodiment executed by the controller 41 includes the following processing. First ultrasonic image data (intermediate processed image) based on a reception signal for image generation received by an ultrasonic probe 20 and first correct answer data (probability distribution image A1) to second ultrasonic image data (diagnostic image P2) obtained by performing intermediate processing including coordinate transformation to the first ultrasonic image data are acquired. Second correct answer data (probability distribution image A2) is obtained by performing inverse transformation of coordinate transformation on the first correct answer data. A pair of the first ultrasonic image data before the intermediate processing and the second correct answer data is stored in the storage section 45 as learning data for machine learning. According to such a method of generating learning data, the learning data 452 for obtaining the learning model 1521 with which a more accurate output result is obtained without increasing user's workload so much is obtained.

Further, the learning data creation program 453 according to the present embodiment causes a computer (electronic calculator 40) to execute an acquisition function of acquiring first ultrasonic image data (intermediate processed image P1) based on a reception signal for image generation received by the ultrasonic probe 20 and first correct answer data (probability distribution image A1) for second ultrasonic image data (diagnostic image P2) obtained by performing intermediate processing including coordinate transformation on the first ultrasonic image data, an inverse transformation function of performing inverse transformation of the coordinate transformation on the first correct answer data to obtain second correct answer data (probability distribution image A2), and a storage control function of storing a pair of the first ultrasonic image data and the second correct answer data before the intermediate processing in the storage section 45 as the learning data 452 for machine learning.

By causing the electronic calculator 40 to execute the learning data creation program 453, the user can easily create the learning data 452 from the imaging data of the ultrasonic diagnostic apparatus 1 without requiring a special configuration.

Note that the present disclosure is not limited to the above-described embodiments, and various modifications are possible.

For example, in the above-described embodiment, the B-mode image is described as an example of the diagnostic image, but the present invention is not limited thereto. The diagnostic image may be another image, for example, an M-mode image, an image indicating an analysis result of color Doppler, power Doppler, elastography, or the like.

Although it has been described in the aforementioned embodiment that the interpolation between the pixels is performed along with the coordinate transformation, the present invention is not limited thereto. In the case of a linearly scanned image with an appropriate focal length or the like, interpolation is not necessary. Furthermore, the coordinate transformation may include transformation other than transformation by DSC.

Although it has been described in the above embodiment that the correct answer data is data in which a contour shape or a region is set, the present invention is not limited thereto. The correct answer data may be specific coordinate data. Alternatively, the correct answer data may be a calculated physical quantity, for example, a length (a circumferential length, a width of a specific component, a distance between specific positions, or the like), an area, or a volume of the aforementioned outline shape.

Although the transformation parameters of the coordinate transformation are described as being determined based on the transmission direction information of the ultrasonic waves included in the header data such as the intermediate processed image P1 in the above embodiment, there is no limitation thereto. Scanning information or the like of the ultrasonic probe 20 may be separately acquired from the outside of the image, and the transformation parameter may be determined based on the scanning information or the like. The scanning information in this case may not be appended to each of the individual intermediate processed images P1. Only the scanning information on a part of the reference images may be acquirable. The transformation parameter may be determined by, for example, a combination of information for obtaining the amount of change in the output direction of ultrasonic waves according to the time difference between each image and the reference image or the number of frames therebetween and the scanning information of the reference image.

In the above embodiment, it has been described that the image before the coordinate transformation input to the learning model 1521 is the intermediate processed image P1, that is, the image before, during, or after the intermediate processing excluding the coordinate transformation. However, the RF data before the detection processing is performed further back may be the data input to the learning model 1521. That is, the processing including the coordinate transformation may include detection processing.

Although the CNN is used as the image recognition algorithm of the machine learning model 451 (the learning model 1521) in the above embodiment, there is no limitation thereto. Any other algorithm by which the shape and/or structure of a detection object may be learned and identifiable may be utilized by the machine learning model 451, such as a support vector machine.

The ultrasonic diagnostic apparatus 1 is not limited to a medical apparatus that emits ultrasonic waves to a human body. The subject of the ultrasonic diagnostic apparatus 1 may be a living being other than a human, such as a pet, or may be one used for inspection of the internal structure of a structure.

The configuration of the main body section 10 of the ultrasonic diagnostic apparatus 1 may be achieved by a combination (system) of a plurality of devices. For example, the operation acceptance section 18 and the display part 19 may be attached as peripheral devices. Some of the processes of the processing section 152, the coordinate transformation section 153, and the like in the main body section 10 may be transmitted to an external electronic calculator or the like and separately performed. Alternatively, in the main body section 10, the first half of processing (processing as a reception apparatus) such as signal amplification and envelope detection and the second half of processing (processing as an image diagnostic apparatus) such as detection may be completely separated and may be performed by a plurality of different apparatuses.

In the aforementioned embodiment, the learning of the machine learning model 451 and the creation of the learning data 452 are performed by the electronic calculator 40 separate from the ultrasonic diagnostic apparatus 1. However, the ultrasonic diagnostic apparatus 1 may perform learning and creation of the learning data 452. In this case, a learning data creation program 453 is stored in the storage section 151. Alternatively, the learning of the machine learning model 451 and the creation of the learning data 452 may be executed by separate electronic calculators. Furthermore, the learning data 452 may be stored not in the storage section 45 of the electronic calculator 40 but in a storage section such as an external network storage, an external storage device, or a cloud server (database device).

In the above description, as a computer-readable medium that stores the learning data creation program 453 for controlling creation of learning data of the present disclosure and a computer-readable medium that stores the diagnostic program 1511 for diagnosing an ultrasonic image, the storage sections 45 and 151 including a nonvolatile memory such as an HDD and a flash memory have been described as examples, but the present disclosure is not limited thereto. As other computer-readable media, other nonvolatile memories such as an MRAM, or portable recording media such as a CD-ROM and a DVD disk can be applied. Furthermore, a carrier wave is also applied to the present disclosure as a medium for providing the data of the program of the present disclosure via a communication line.

In addition, the specific configuration, the content and the procedure of the processing operation, and the like described in the above-described embodiment can be appropriately changed without departing from the spirit and scope of the present disclosure. The scope of the present invention includes the scope of the invention described in the claims and the equivalent scope thereof.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A non-transitory storage medium storing a computer-readable diagnostic program that causes a hardware processor of a computer to execute a learning model, wherein the learning model is machine-learned using learning data formed with a pair of:

first ultrasonic image data based on a reception signal for image generation received by an ultrasonic probe from an object; and second correct answer data, wherein the second correct answer data is obtained by generating second ultrasonic image data by performing coordinate transformation on the first ultrasonic image data, obtaining a first correct answer by input from a user viewing the second ultrasonic image data, and acquiring the second correct answer data from an inverse transformation of the first correct answer data;

wherein the hardware processor executes the learning model by:

obtaining a third ultrasonic image data based on a reception signal that is received by the ultrasonic probe and is intermediate image data that has not been subjected to processing including the coordinate transformation; and causing the learning model to output a first inference result from the third ultrasonic image data using the learning model, wherein the first inference result includes a probability distribution image representing the probability of being a range of a structure, the probability distribution image is subjected to the coordinate transformation, and a characteristic value of the structure is calculated from the probability distribution image after the coordinate transformation.

2. The storage medium according to claim 1, wherein the second ultrasonic image data is a B-mode image.

3. The storage medium according to claim 1, wherein the coordinate transformation includes interpolation between pixels.

4. The storage medium according to claim 1, wherein the first correct answer data is inversely transformed based on transmission direction information of an ultrasonic wave.

5. An ultrasonic diagnostic apparatus comprising:

an ultrasonic probe that transmits and receives ultrasonic waves to and from a subject;

a hardware processor; and a learning model, wherein the learning model is machine-learned using learning data formed with a pair of:

first ultrasonic image data based on a reception signal for image generation received by the ultrasonic probe from an object; and second correct answer data, wherein the second correct answer data is obtained by generating second ultrasonic image data by performing coordinate transformation on the first ultrasonic image data, obtaining a first correct answer by input from a user viewing the second ultrasonic image data, and acquiring the second correct answer data from an inverse transformation of the first correct answer data;

wherein the hardware processor executes the learning model by:

obtaining a third ultrasonic image data based on a reception signal that is received by the ultrasonic probe and is intermediate image data that has not been subjected to processing including coordinate transformation; and causes the learning model to output a first inference result from the third ultrasonic image data, wherein the first inference result includes a probability distribution image representing the probability of being a range of a structure, subjects the probability distribution image to the coordinate transformation, and calculates a characteristic value of the structure from the probability distribution image after the coordinate transformation.

6. The ultrasonic diagnostic apparatus according to claim 5, wherein the hardware processor performs the coordinate transformation on the first inference result to obtain a second inference result, and outputs the second inference result after the coordinate transformation.

7. The ultrasonic diagnostic apparatus according to claim 5, wherein the second ultrasonic image data is a B-mode image.

8. The ultrasonic diagnostic apparatus according to claim 5, wherein the coordinate transformation includes interpolation between pixels.

9. The ultrasonic diagnostic apparatus according to claim 5, wherein the first correct answer data is inversely transformed based on transmission direction information of an ultrasonic wave.

10. The ultrasonic diagnostic apparatus according to claim 6, wherein the hardware processor performs the coordinate transformation that is determined based on transmission direction information of an ultrasonic wave on the first inference result to obtain a second inference result, and outputs the second inference result after the coordinate transformation.

11. The ultrasonic diagnostic apparatus according to claim 10, wherein the transmission direction information of the ultrasonic wave is provided to the first ultrasonic image data.

12. The ultrasonic diagnostic apparatus according to claim 6, further comprising a display part capable of displaying the second inference result.

13. The ultrasonic diagnostic apparatus according to claim 6, wherein the hardware processor combines a plurality of images related to the second inference result.

14. The ultrasonic diagnostic apparatus according to claim 6, wherein the hardware processor binarizes or classifies the second inference result or applies a look-up table to the second inference result.

15. The ultrasonic diagnostic apparatus according to claim 6, wherein the hardware processor binarizes the second inference result, and estimates at least one of a position, an area, a volume, a length, a height, a width, a depth, and a diameter associated with a target of interest of the subject based on the binarized inference result.

16. An ultrasonic diagnostic system comprising:

an ultrasonic probe that transmits and receives ultrasonic waves to and from a subject;

a hardware processor; and a learning model, wherein the learning model is machine-learned using learning data formed with a pair of:

first ultrasonic image data based on a reception signal for image generation received by the ultrasonic probe from an object; and second correct answer data, wherein the second correct answer is obtained by generating second ultrasonic image data by performing coordinate transformation on the first ultrasonic image data, obtaining a first correct answer by input from a user viewing the second ultrasonic image data, and acquiring the second correct answer data from an inverse transformation of the first correct answer data;

wherein the hardware processor executes the learning model by:

obtaining a third ultrasonic image data being based on a reception signal that is received by the ultrasonic probe and is intermediate image data that has not been subjected to processing including coordinate transformation, and causing the learning model to output a first inference result from the third ultrasonic image data, wherein the first inference result includes a probability distribution image representing the probability of being a range of a structure, subjects the probability distribution image to the coordinate transformation, and calculates a characteristic value of the structure from the probability distribution image after the coordinate transformation.

17. The ultrasonic diagnostic apparatus according to claim 5, wherein inverse transformation of other than the coordinate transformation is not performed on the first correct answer data.

18. The ultrasonic diagnostic apparatus according to claim 5, wherein the learning data is formed with a plurality of pairs of the first ultrasonic image data and each of a plurality of the second correct answer data, and the plurality of the second correct answer data is obtained by performing:

generating a plurality of ultrasonic image data by processing a plurality of types of processes including coordinate transformation on the first ultrasonic image data;

merging the plurality of ultrasonic image data to generate the second ultrasonic image data; and processing a plurality of different inverse transformations of coordinate transformation on the first correct answer data for the second ultrasonic image data.

19. The ultrasonic diagnostic apparatus according to claim 5, wherein generating a plurality of ultrasonic image data by processing a plurality of types of processes including coordinate transformation on the first ultrasonic image data;

merging the plurality of ultrasonic image data to generate the second ultrasonic image data;

processing a plurality of different inverse transformations of coordinate transformation on the first correct answer data for the second ultrasonic image data to generate a plurality of the second correct answer data; and selecting an answer data among the plurality of the second correct answer data.

20. The ultrasonic diagnostic apparatus according to claim 5, wherein the hardware processor applies a look-up table to the second inference result to change a luminance value distribution of the second inference result to a luminance value distribution that is easily viewable on a display screen.

* * * * *